United States Patent
Wei et al.

(10) Patent No.: US 6,422,701 B2
(45) Date of Patent: Jul. 23, 2002

(54) VISUAL FIELD TESTER

(75) Inventors: Jay Wei, Fremont; Zheng-wu Li, Dublin; Shiyu Zhang, Hayward, all of CA (US)

(73) Assignee: Carl Zeiss, Inc., Thornwood, NY (US)

( * ) Notice: Subject to any disclaimer, the term of this patent is extended or adjusted under 35 U.S.C. 154(b) by 0 days.

(21) Appl. No.: 09/928,164

(22) Filed: Aug. 10, 2001

Related U.S. Application Data

(63) Continuation of application No. 09/637,849, filed on Aug. 10, 2000, now abandoned.

(51) Int. Cl.[7] ............................................. A61B 3/02
(52) U.S. Cl. ........................................................ 351/243
(58) Field of Search ................................ 351/205, 206, 351/201, 211, 212, 213, 215, 224, 226, 237, 239, 243; 345/7; 356/479; 382/114, 274; 348/62, 63

(56) References Cited

U.S. PATENT DOCUMENTS 5,359,675 A  * 10/1994 Siwoff .......................... 382/114

* cited by examiner

*Primary Examiner*—George Manuel
(74) *Attorney, Agent, or Firm*—Michael B. Einschlag

(57) ABSTRACT

One embodiment of the present invention is a visual field tester that includes: (a) a high intensity light source; (b) an optical fiber; (c) scanning optics, wherein light output from the light source is directed by the optical fiber to impinge upon the scanning optics, and the scanning optics directs the light to form a stimulus at various field positions; and (d) a video display system to output one or more light patterns. Another embodiment of the present invention is a visual field tester that includes: (a) a video display system to output one or more types of light patterns; (b) a background illumination display system; and (c) viewing optics to magnify the field of view of the video display system and the background illumination display system. Still another embodiment of the present invention is a visual field tester that includes: (a) a video display system to output one or more types of light patterns; and (b) a background illumination display system that outputs variable intensity light, wherein the video display system includes: (i) a variable intensity, high brightness light source and (ii) a light modulator display disposed to transmit light output from the source.

57 Claims, 3 Drawing Sheets

100

VISUAL FIELD TESTER

This is a continuation of Ser. No 09/637,849 filed Aug. 10, 2000 now abandoned.

TECHNICAL FIELD OF THE INVENTION

The present invention pertains to method and apparatus for performing visual field tests. In particular, the present invention relates to method and apparatus for performing video-based visual field tests and stimuli-contrast visual field tests.

BACKGROUND OF THE INVENTION

As is well known, methods of testing human visual functions include determinations of: (a) contrast sensitivity; (b) flicker frequency sensitivity; (c), visual resolution acuity; and (d) color sensitivity. Apparatus that can carry out such tests are referred to as automatic perimeters or visual field testers, and such apparatus have been known in the art for many years.

A Standard Automatic Perimeter (SAP) that is known in the art and is used to perform a contrast sensitivity test includes a hemispherical projection surface and a stimulus optical projection system. In a typical such SAP, the hemispherical projection surface is uniformly illuminated (using a white light source) to provide a constant and uniform background illumination, and the stimulus optical projection system projects a circular spot on the hemispherical projection surface to provide a stimulus to the human vision. The radius of the hemispherical projection surface is about 30 cm to enable the subject to see the stimulus comfortably (i.e., without straining the subject's test eye), and the position and brightness of the stimulus are specified by a computer implemented algorithm. In use, a subject is asked to respond to the stimulus by pressing, for example, a mouse button, and the contrast sensitivity of the subject's visual field is mapped by changing the brightness and position of the stimulus on the constant, uniform background illumination.

U.S. Pat. No. 5,323,194 discloses an SAP having reduced size in a peripheral field region. This reduced size is produced by changing the shape of the projection surface from a hemisphere to a hemisphere. However, a central field region still uses the same distance from the subject as is used in the hemispherical SAP.

U.S. Pat. No. 5,046,835 discloses that the size of an SAP can be reduced by using a cupola-less optical system. In such a cupola-less optical system, the stimulus is presented to the subject by illuminating a diaphragm with light output from an LED, a halogen lamp, or a laser light source while the background is illuminated with light output from a diffused light source. The stimulus and background are combined, and projected onto the subject's retina to perform the visual field test.

Despite the above-described improvements, presently available SAPs can only perform static contrast sensitivity tests. This is because: (a) the speed of the optical projection system is limited; (b) mechanical movement of a diaphragm of the SAP is too slow to generate a video-based visual test pattern; and (c) it is impossible to generate a video-based visual test pattern since background illumination is provided by a diffused light source.

A flicker frequency sensitivity visual field test requires a video system to generate a high frequency test pattern. One commercially available flicker frequency sensitivity visual field tester is called a Frequency Doubling Technology ("FDT") Visual Field Instrument. The FDT tester includes a cathode ray tube ("CRT") and viewing optics to display a high frequency test pattern with a forty (40) degree field of view. However, due to brightness limitations of current CRTs, and limitations in the field of view of the viewing optics, the FDT tester cannot perform a contrast sensitivity test like that performed by the SAP.

In light of the above-described limitations, there is a need in the art for an apparatus that is relatively small in physical size, and is capable of performing: (a) a contrast sensitivity test; (b) a flicker frequency sensitivity test; and (c) other visual field tests that require a video test pattern (for example, a visual resolution acuity test).

SUMMARY OF THE INVENTION

Embodiments of the present invention advantageously satisfy the above-identified need in the art, and provide an apparatus that is relatively small in physical size. and is capable of performing: (a) a contrast sensitivity test; (b) a flicker frequency sensitivity test; and (c) other visual field tests that require a video test pattern (for example, a visual resolution acuity test).

Specifically, a first embodiment of the present invention is a visual field tester that comprises: (a) a high intensity light source; (b) an optical fiber; (c) scanning optics, wherein light output from the light source is directed by the optical fiber to impinge upon the scanning optics, and the scanning optics directs the light to form a stimulus at various field positions; and (d) a video display system to output one or more light patterns.

A second embodiment of the present invention is a visual field tester that comprises: (a) a video display system to output one or more types of light patterns; (b) a background illumination display system; and (c) viewing optics to magnify the field of view of the video display system and the background illumination display system.

A third embodiment of the present invention is a visual field tester that comprises: (a) a video display system to output one or more types of light patterns; and (b) a background illumination display system that outputs variable intensity light, wherein the video display system comprises: (i) a variable intensity, high brightness light source and (ii) a light modulator display disposed to transmit light output from the source. In accordance with a further variation of this embodiment, the visual field tester further comprises a controller to control the variable intensity, high brightness light source and the background illumination display system.

DETAILED DESCRIPTION

Figure 1A:
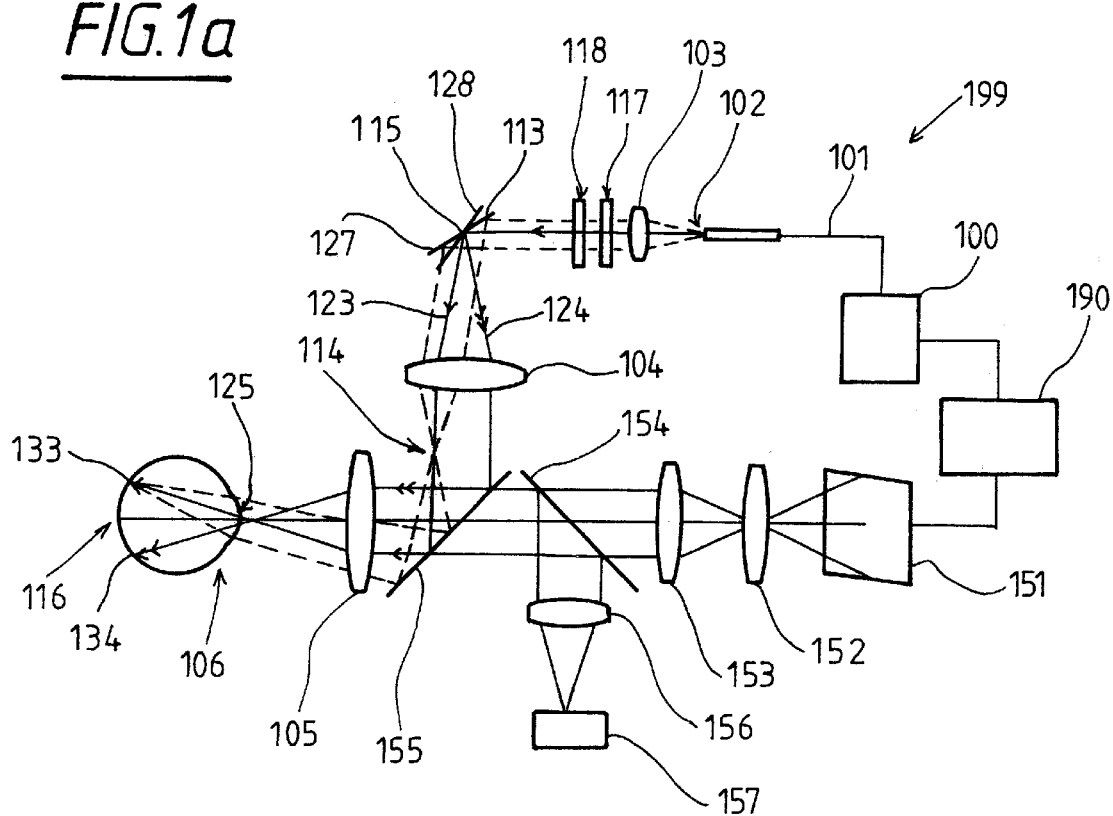
FIG. 1A shows a block diagram of a visual field tester that is fabricated in accordance with one embodiment of the present invention.

FIG. 1A shows a block diagram of visual field tester 199 that is fabricated in accordance with one embodiment of the present invention. As shown in FIG. 1, white light output from light illumination box 100 impinges upon, and is guided through, optical fiber 101. In one embodiment of the present invention, light illumination box 100 is a high intensity white light source that comprises, for example and without limitation, a light box which uses anyone of a number of lamps that are well known to those of ordinary skill in the art such as, for example and without limitation, a Halogen lamp, a short arc Mercury lamp, a Xenon lamp, and so forth.

As further shown in FIG. 1, end 102 of optical fiber 101 is imaged by an imaging system (the imaging system comprises lens system 103, scanner 127, lens system 104, and lens system 105) onto retina 116 of subject's eye 106 to form a stimulus. Although lens systems 103–105 are each shown as a single lens, those of ordinary skill in the art will readily understand that each of lens systems 103–105 may comprise one or more lenses. Since the emitting area of end 102 of fiber 101 is small (i.e., typically having a lateral cross-sectional dimension in a range from about 5 microns to about several tens of microns), the lateral cross-sectional dimension of lens systems 103–105 can be small (this is because the effective lateral cross-sectional dimension of lens systems 103–105 is linearly proportional to the lateral cross-sectional area of the core of end 102 of optical fiber 101). As a result, one can reduce the required size of lens systems 103–105 by using an optical fiber having a small core size. However, note that, as the cross-sectional area of the core of optical fiber 101 decreases, one would need to increase the intensity of light illumination box 100 because it is typically more difficult to couple light into a smaller optical fiber core.

In accordance with one such embodiment of the present invention, the position of lens system 103 is adjustable along its optical axis to enable visual field tester 199 to accommodate refraction error of subject's eye 106. In one embodiment of the present invention, the magnification of the lens system comprising lens systems 103–105 is designed so that the cross-sectional area of the core of optical fiber 101 subtends a 0.43 degree field of view ("FOV") at eye 106; a 0.43 degree FOV bright spot is the most frequently used stimulus size in SAP tests (such a stimulus is referred to in the art as a size III stimulus). To provide stimuli having different sizes, one can place a diaphragm, for example and without limitation, on the focal plane of lens system 103. Then, end 102 of optical fiber 101 would be placed behind the diaphragm, for example, to fully illuminate an aperture of the diaphragm. In accordance with such an embodiment, the size of the aperture could be adjustable in accordance with any one of a number of methods that are well known to those of ordinary skill in the art to provide stimuli having different sizes.

Apparatus for providing a fixation target or for fixing the position of a subject's eye can be fabricated using any one of a number of methods that are well known to those of ordinary skill in the art. Such apparatus are not shown in FIGS. 1A, 2 or 3 so that the operation of the remainder of the disclosed apparatus can more easily be understood.

As further shown in FIG. 1A, the stimulus (i.e., the image of end 102 of optical fiber 101) is moved under the control of computer 190 to impinge on different positions in the visual field by use of computer-controlled scanner 127. As shown in FIG. 1A, computer-controlled scanner is implemented as gimbal-mounted mirror 127. Many methods are well known to those of ordinary skill in the art for use in fabricating a computer-controlled scanner, and in particular, a computer-controlled gimbal-mounted mirror. Whenever computer 190 causes gimbal-mounted mirror 127 to be oriented along position 113 shown in FIG. 1A, output from end 102 of optical fiber 101 travels along optical path 123, and impinges (as a stimulus) upon retina 116 at location 133. Whenever computer 190 causes gimbal-mounted mirror 127 to be oriented along position 128 shown in FIG. 1A, output from end 102 of optical fiber 101 travels along optical path 124, and impinges (as a stimulus) upon retina 116 at location 134. In addition, gimbal-mounted mirror 127 is located so that pivot point 115 thereof is imaged at the center of pupil 125 of eye 106. In accordance with one such embodiment of the present invention, when the optical design of the imaging system is such that a combination of the numerical aperture of the core of optical fiber 101 (i.e., a measure of the angle of divergence of the beam of light emerging from the core of optical fiber 101) and the focal lengths of lens systems 103–105 yield a beam size of about 12 mm on the cornea of eye 106 (which beam size is large enough to overfill pupil 125 of eye 106), the subject can move eye 106 without seeing a brightness change in the stimulus.

As further shown in FIG. 1A, variable neutral density ("ND") filter 117 is controlled by computer 190 to vary the intensity of the stimulus. Variable ND filter 117 is used (together with optional color filter 118) to select a portion of the spectrum of light output from end 102 of fiber 101 to provide a stimulus for a color contrast test. In a preferred embodiment of the present invention, variable neutral density ("ND") filter 117 is a variable ND filter wheel that rotates in response to input from computer 190, and color filter 118 is a color filter wheel that rotates in response to input from computer 190. Many methods are well known to those of ordinary skill in the art for fabricating embodiments of variable neutral density filter 117 and color filter wheel 118. Note, although optional color filter 118 is shown in FIG. 1A, it may be omitted to provide certain visual field tests not requiring a colored stimulus. Alternatively, color filter 118 may be fabricated in accordance with any one of a number of methods that are well known to those of ordinary skill in the art to include settings or positions (for example, in a color wheel configuration) that do not affect radiation passing therethrough for use in performing visual field tests not requiring a colored stimulus.

In an alternative to the embodiment shown in FIG. 1A, the following components: (a) light illumination box 100; (b) optical fiber 101; (c) lens system 103; (d) variable neutral density filter 117; (e) scanner 127; and (f) lens system 104 can be replaced by a high brightness mini-CRT video system display (commercially available, for example, from Thompson Electronics, Inc. of France) or a micro display device (although a micro display device that has only one liquid crystal light modulator/linear polarizer panel may be used, it is preferred to use a high contrast embodiment of a micro display device that is described in detail below in conjunction with FIGS. 4 and 5). In such an embodiment, the high brightness CRT or the micro display device would be placed at plane 114, and each would require a minimum output intensity of 1500 foot-Lamnbert for an SAP test. In such an embodiment, optional color filter 118 may be placed in the optical path of the output from these devices to enable a color sensitivity test.

As further shown in FIG. 1A, micro-display 151 is a video system display, for example and without limitation, a mini-CRT video system display (for example, a high brightness mini-CRT video system display), a liquid crystal display ("LCD") video system display, a micro display device, or any other type video system display. As shown in FIG. 1A, micro-display 151 is optically conjugated to retina 116 through an optical system which comprises lens system 152, lens system 153, beamsplitter 154, beamsplitter 155, lens system 105, and eye 106. Although lens systems 152, 153, and 105 are each shown as a single lens, those of ordinary skill in the art will readily understand that each of lens systems 152, 153, and 105 may comprise one or more lenses.

In accordance with this embodiment of the present invention, micro-display 151 can be used to present uniform illumination for performing a color contrast sensitivity test or an SAP test. In addition, micro-display 151 can also present an FDT type video pattern with variable frequency for performing a flicker frequency sensitivity test. Lastly, micro-display 151 can also present different resolution acuity targets for performing a visual resolution acuity test. In accordance with this embodiment of the present invention, the particular choice of display output provided is determined, for example and without limitation, by user input to computer 190 in accordance with any one of a number of methods that are well known to those of ordinary skill in the art. In accordance with such an embodiment, computer 190 sends appropriate video signals to micro-display 151 in accordance with any one of a number of methods that are well known to those of ordinary skill in the art to cause micro-display 151 to present the desired output.

In an embodiment using a micro display device, a variable neutral density filter may be placed in the illumination path of the micro display device to control the intensity of the illumination output from the micro display device. In yet another embodiment where micro-display 151 is used to present a uniform background illumination, for example, for performing an SAP test, micro-display 151 can be a low brightness mini-CRT video system display (for example, a mini-CRT video system display having a 100 to 200 foot-Lambert output may be used since it is not being used to generate a stimulus, and as a result, the brightness requirement is significantly reduced), or a light box with variable output illumination intensity.

As further shown in FIG. 1A, CCD camera 157 is optically conjugated to the subject's cornea through an optical system which comprises CCD lens system 156, beamsplitter 154, beamsplitter 155, and lens system 105. Although CCD lens system 156 and lens system 105 are each shown as a single lens, those of ordinary skill in the art will readily understand that each of CCD lens system 156 and lens system 105 may comprise one or more lenses. This configuration may be used to align the subject's eye at the beginning of a test using a fixation target (not shown) in accordance with any one of a number of methods that are well known to those of ordinary skill in the art, and to monitor the subject's eye motion (for example, deviation from a viewing direction) during the test in accordance with any one of a number of methods that are well known to those of ordinary skill in the art.

Advantageous aspects of the embodiment of the present invention shown in FIG. 1A arise from the fact that: (a) since the stimulus is generated using a single bright optical fiber light source, it is possible to achieve a 10,000 asb brightness standard in an SAP test; and (b) since background illumination provided by micro-display device 151 is independent of the stimulus, contrast issues are minimized. A further advantage of the embodiment of the present invention shown in FIG. 1A arises from the fact that whenever light illumination box 100 is turned off, visual field tester 199 functions like a virtual display with a wide FOV that is suitable for a visual field test. For example, using an embodiment wherein micro-display 151 is a mini-CRT video system or a micro display device one can produce a virtual image having a FOV that is more than 60 degrees, for example, by embodying lens system 105 as a wide angle eye piece. This is to be contrasted with commercial FDT testers and other video based testers that have less a FOV that is less than 40 degrees, which FOV is limited by the size of the CRT used.

Figure 1B:
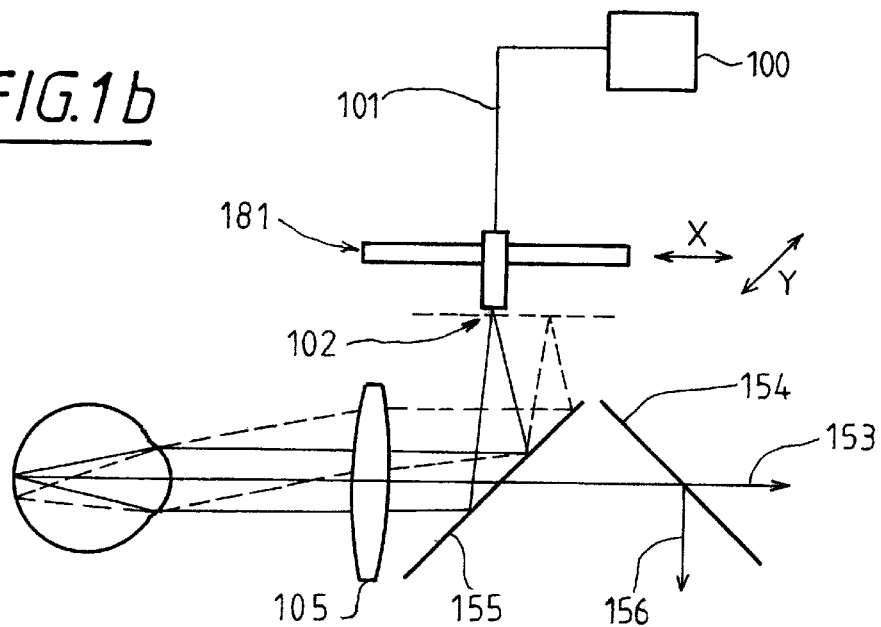
FIG. 1B shows a block diagram of an alternative apparatus for use in generating a stimulus in the visual field tester shown in FIG. 1.

FIG. 1B shows a block diagram of an alternative apparatus for use in generating a stimulus that can be used in visual field tester 199 shown in FIG. 1. The apparatus shown in FIG. 1B replaces a scanning optics path in FIG. 1A that comprises lens system 103, scanning mirror 127, and lens system 104. As shown in FIG. 1B, optical fiber to 101 is mounted on an X-Y translational stage 181 that operates in response to input from computer 190 in a manner which is well known to those of ordinary skill in the art. As further shown in FIG. 1B, end 102 of optical fiber 101 is located at a back focal plane of lens system 105 so that illumination output from end 102 will impinge upon retina 116 of eye 106 to provide the stimulus. As one can readily appreciate form this, moving stage 181 (for example, moving stage 181 in response to input from computer 190) causes the stimulus to be presented at different locations of the visual field. Advantageously, since there is no scanning optics in front of illumination exiting from end 102 of optical fiber 101, reflection from scanning optics will be reduced, and the contrast ratio of the optical system will be enhanced. A lens system that may be used advantageously in implementing lens system 105 is a wide angle, long eye relief, and large exit pupil eyepiece lens design such as the well known Erfle eyepiece.

Figure 2:
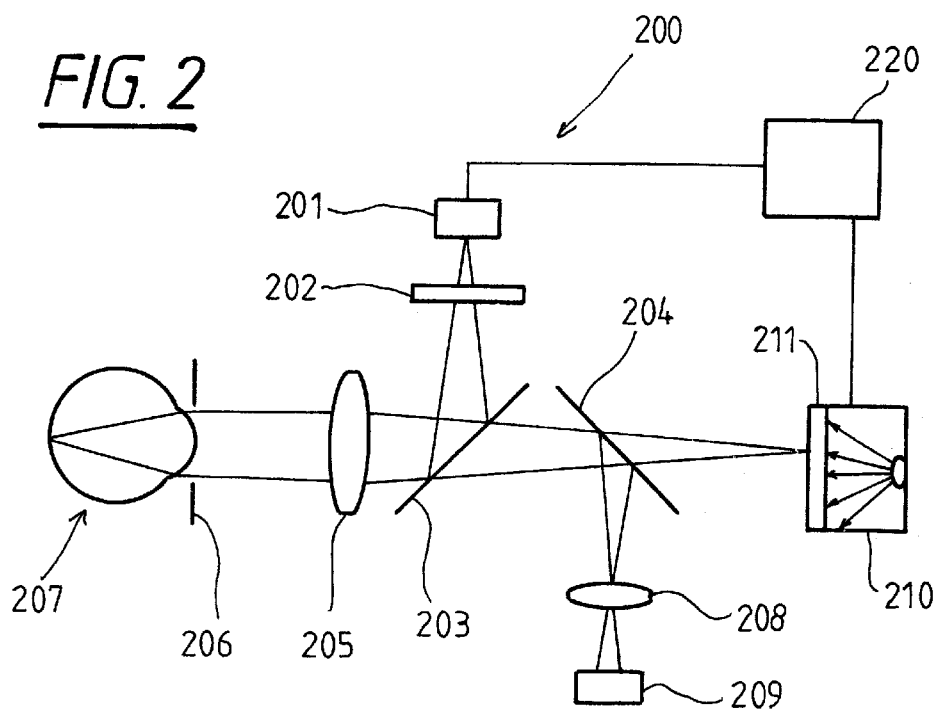
FIG. 2 shows a block diagram of a visual field tester that is fabricated in accordance with another embodiment of the present invention.

FIG. 2 shows a block diagram of visual field tester 200 that is fabricated in accordance with another embodiment of the present invention. As shown in FIG. 2, visual field tester 200 comprises high intensity video system display 201 such as, for example and without limitation, a high intensity mini-CRT video system display, or a micro display device. In accordance with this embodiment of the present invention, video system display 201 produces a bright spot (for example and without limitation, a round spot) as the stimulus, which spot is surrounded by a uniform background for an SAP test. In addition, video system display 201 can generate an FDT type video pattern with a variable frequency, different resolution acuity targets, and other test patterns for video type visual field testing. In accordance with this embodiment of the present invention, the particular choice of display output provided is determined, for example and without limitation, by user input to computer 220 in accordance with any one of a number of methods that are well known to those of ordinary skill in the art. In accordance with such an embodiment, computer 220 sends appropriate video signals to video system display 201 in accordance with any one of a number of methods that are well known to those of ordinary skill in the art to cause video system display 201 to present the desired output.

To perform a color contrast test, optional color filter 202 selects a portion of the spectrum of light output from video system display 201 to provide a stimulus, and illumination output from light box 210 (in response to input from computer 220) passes through filter 211 to provide an appropriately colored background. Filter 211 may be a color filter (like color filter 118) that can vary the color of the background, or it can be a static color filter. In a preferred embodiment of the present invention, optional color filter 202 is a color filter wheel that rotates in response to input (not shown) from computer 220. Note, although optional color filter 202 is shown in FIG. 2, it may be omitted to provide certain visual field tests not requiring a colored stimulus. Alternatively, color filter 202 may be fabricated in accordance with any one of a number of methods that are well known to those of ordinary skill in the art to include settings or positions (for example, in a color wheel configuration) that do not affect radiation passing therethrough for use in performing visual field tests not requiring a colored stimulus.

As further shown in FIG. 2, CCD camera 209 is optically conjugated to the subject's cornea through an optical system which comprises CCD lens system 208, beamsplitter 204, beamsplitter 205, and lens system 205. Although CCD lens system 208 and lens system 205 are each shown as a single lens, those of ordinary skill in the art will readily understand that each of CCD lens system 208 and lens system 205 may comprise one or more lenses. This configuration may be used to align the subject's eye at the beginning of a test using a fixation target (not shown) in accordance with any one of a number of methods that are well known to those of ordinary skill in the art, and to monitor the subject's eye motion (for example, deviation from a viewing direction) during the test in accordance with any one of a number of methods that are well known to those of ordinary skill in the art.

As shown in FIG. 2, output from high intensity video system display 201 and from light box 210 are projected through lens system 205 to the subject's retina. In accordance with one such embodiment of the present invention, lens system 205 is an inverted telephoto lens. As is well known to those of ordinary skill in the art, an inverted telephoto lens has an effective focal length that is longer than its back focal length. Consequently, its entrance pupil is located outside of the physical aperture of its first lens element. Lens system 205 can also be embodied as an eyepiece lens system that has its entrance pupil located in front of the first lens of the eyepiece lens system. In accordance with this embodiment of the present invention, the subject's head is placed in a fixture (not shown) so that the pupil of eye 207 is located at entrance pupil 206 of lens system 205. Such a fixture may be fabricated in accordance with any one of a number of methods that are well known to those of ordinary skill in the art. Advantageously, in accordance with this embodiment of the present invention, the field of view of display 201 and light box 210 can be viewed without vignetting.

In accordance with this embodiment of the present invention, beamsplitter 203 can optimized (in accordance with any one of a number of methods that are well known to those of ordinary skill in the art) for transmission/reflection percentage for white light (for use in an SAP test) or it can be a dichroic beamsplitter for use in a color contrast test. In addition, light box 210 can be replaced with a micro display device to provide background illumination.

Figure 3:
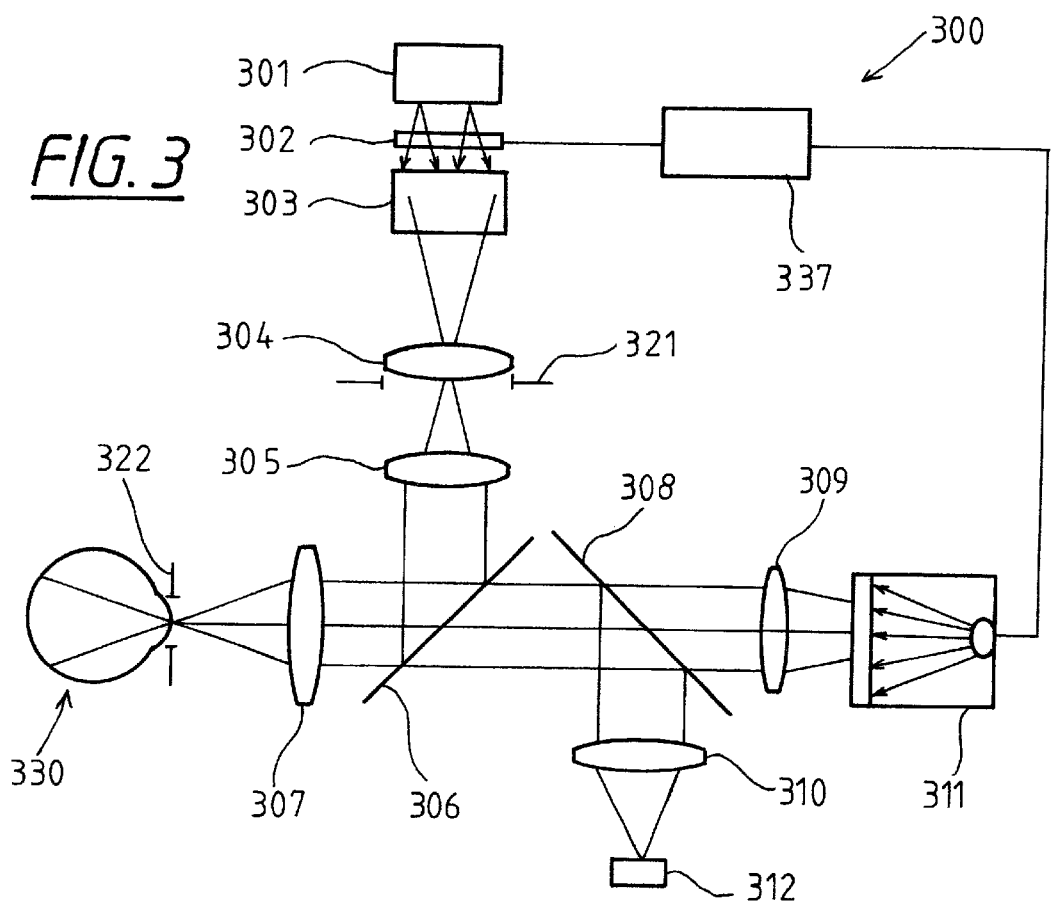
FIG. 3 shows a block diagram of a visual field tester that is fabricated in accordance with yet another embodiment of the present invention.

FIG. 3 shows a block diagram of visual field tester 300 that is fabricated in accordance with another embodiment of the present invention. As shown in FIG. 3 high brightness back illuminator 301, for example and without limitation, a fluorescent lamp, a LED array, a halogen lamp and so forth, outputs radiation that passes through variable neutral density filter 302, and impinges upon mini-display 303. The intensity of the radiation that impinges upon mini-display 303 is determined by variable neutral density filter 302 in response to input from computer 337. In accordance with this embodiment of the present invention, mini-display 303 is a transmissive-type light modulator display such as, for example and without limitation, a liquid crystal display ("LCD"), and preferably, a micro display device. Mini-display 303 further comprises, for example and without limitation, an AMLCD driver circuit and a test pattern generator, both of which are well known to those of ordinary skill in the art and both of which are commercially available. Mini-display 303 provides pixel-by-pixel control in response to input from the test pattern generator, which test pattern is determined in response to input from computer 337 in accordance with any one of a number of methods that are well known to those of ordinary skill in the art to generate various stimuli.

As is well known to those of ordinary skill in the art, to perform an SAP test, one needs to generate a stimulus having a 50 dB range in intensity level, and a constant background illumination. However, when using an LC-based display issues arise due to the imperfect nature of the LC-based display in an "off" state. This results in background illumination having different intensity levels when the stimulus is generated at different intensity levels. Advantageously, in accordance with this embodiment of the present invention, output from mini-display 303 does not have to provide the background illumination by itself to be useful in performing an SAP test. Instead, in accordance with this embodiment of the present invention, one can achieve the 50 dB range in stimulus intensity level and the constant background illumination by a combination of: (a) the output from mini-display 303; and (b) output from display 311, for example, a light box. To understand how this operates, assume that mini-display 303 has a contrast ratio of 350:1. In this case, whenever a high intensity stimulus is required for a test, variable neutral density filter 302 is adjusted (in response to input from computer 337) so that mini-display 303 will be exposed to light having high enough brightness that mini-display 303 will produce a stimulus having the required high intensity. However, at the same time, mini-display 303 will produce an amount of background illumination that is determined by its contrast ratio (for example, a contrast ratio of 350: 1), and that amount of background illumination may be less than the 31 asb of background illumination required for an SAP test. To correct for this, display 311 (for example and without limitation, a light box) is adjusted (in response to input from computer 337) to cause it to output light having a brightness level such that the sum of background illumination produced by mini-display 303 and background illumination produced by display 311 is 31 asb. On the other hand, whenever a low intensity stimulus is required for a test, variable neutral density filter 302 is adjusted so that mini-display 303 will be exposed to light having enough brightness that mini-display 303 will produce a stimulus having the required low intensity. However, since mini-display 303 may produce background illumination having a brightness level that is only one $350^{th}$ of that of the stimulus, this background illumination brightness level is much less than the 31 asb of background illumination that is required for the SAP test. To correct for this, display 311 is adjusted to cause it to output light having a brightness level such that the sum of background illumination produced by mini-display 303 and background illumination produced by display 311 is 31 asb. The amount of background illumination required for particular values of stimulus intensity can be determined and stored in computer 337 in accordance with any one of a number of methods that are well known to those of ordinary skill in the art. In accordance with one variation of this embodiment, display 311 may be replaced with a micro display device to provide the variable background illumination.

As further shown in FIG. 3, output from mini-display 303 is projected by an imaging system which comprises lens systems 304, 305, and 307 onto the retina of subject 330. Although lens systems 304, 305, and 307 are each shown as a single lens, those of ordinary skill in the art will readily understand that each of lens systems 304, 305, and 307 may comprise one or more lenses. To avoid vignetting, entrance pupil 321 of lens system 304 is conjugated to pupil 322 of eye 330 by lens system 305 and lens system 307.

As further shown in FIG. 3, CCD camera 312 is optically conjugated to the subject's cornea through an optical system which comprises CCD lens system 310, beamsplitter 308, beamsplitter 306, and lens system 307. Although CCD lens system 310 and lens system 307 are each shown as a single lens, those of ordinary skill in the art will readily understand that each of CCD lens system 310 and lens system 307 may comprise one or more lenses. This configuration may be used to align the subject's eye at the beginning of a test using a fixation target (not shown) in accordance with any one of a number of methods that are well known to those of ordinary skill in the art, and to monitor the subject's eye motion (for example, deviation from a viewing direction) during the test in accordance with any one of a number of methods that are well known to those of ordinary skill in the art.

Visual field tester 300 can provide an SAP test, a flicker frequency test, a visual resolution acuity test, and other visual field tests. In accordance with this embodiment of the present invention, the particular choice of display output provided is determined, for example and without limitation, by user input to computer 337 in accordance with any one of a number of methods that are well known to those of ordinary skill in the art. In accordance with such an embodiment, computer 337 sends appropriate video signals to variable neutral density filter 302 and to mini-display 303 in accordance with any one of a number of methods that are well known to those of ordinary skill in the art to cause the desired output to be generated.

Figure 4:
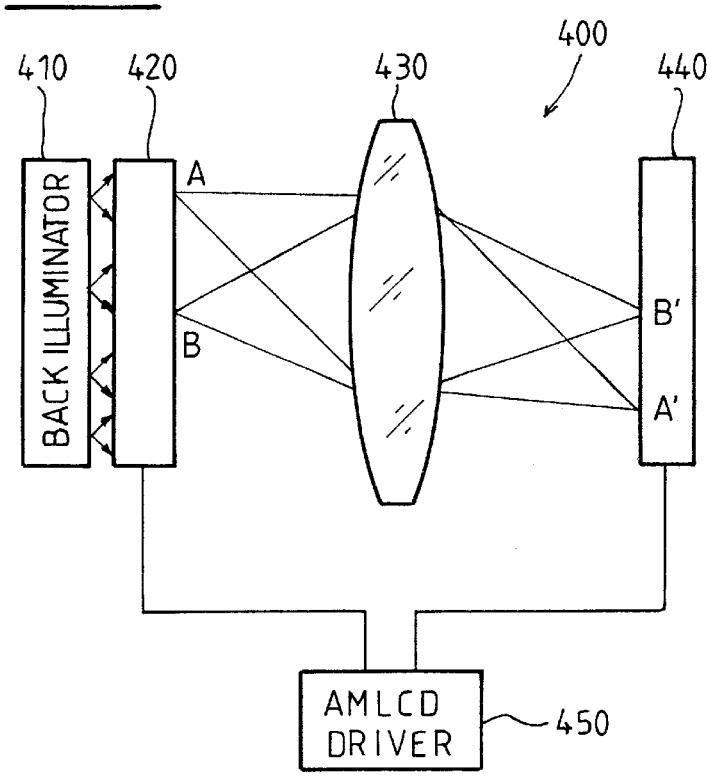
FIG. 4 shows a block diagram of a high contrast, micro display device that is fabricated in accordance with an embodiment of the present invention.

FIG. 4 shows a block diagram of high contrast, micro display device 400 that is fabricated in accordance with an embodiment of the present invention. Advantageously, in accordance with this embodiment of the present invention, micro display device 400 increases the contrast ratio of a Liquid Crystal light modulator ("LC") display. As a result, such a contrast-ratio-enhanced micro display device can be used to fabricate embodiments 199, 200, and 300 described in detail above to improve system performance. As shown in FIG. 4, high contrast, micro display device 400 comprises back illumination system 410 that outputs unpolarized light that impinges upon LC 420. For example and without limitation, back illumination system 410 can be a fluorescent lamp, an LED array, and so forth which provides uniform illumination to LC 420. Light output from LC 420 is relayed by lens system 430 (in one embodiment, lens system 430 has a 1:1 relay ratio) to impinge upon LC 440. Although lens system 430 is shown as a single lens, those of ordinary skill in the art will readily understand that lens systems 430 may comprise one or more lenses. As further shown in FIG. 4, AMLCD driver 450 is a commercial device that modulates LCs 420 and 440 synchronously in a manner that is well known to those of ordinary skill in the art. LCs 420 and 440 are aligned, pixel-to-pixel, so that they can be turned on and off synchronically.

Figure 5:
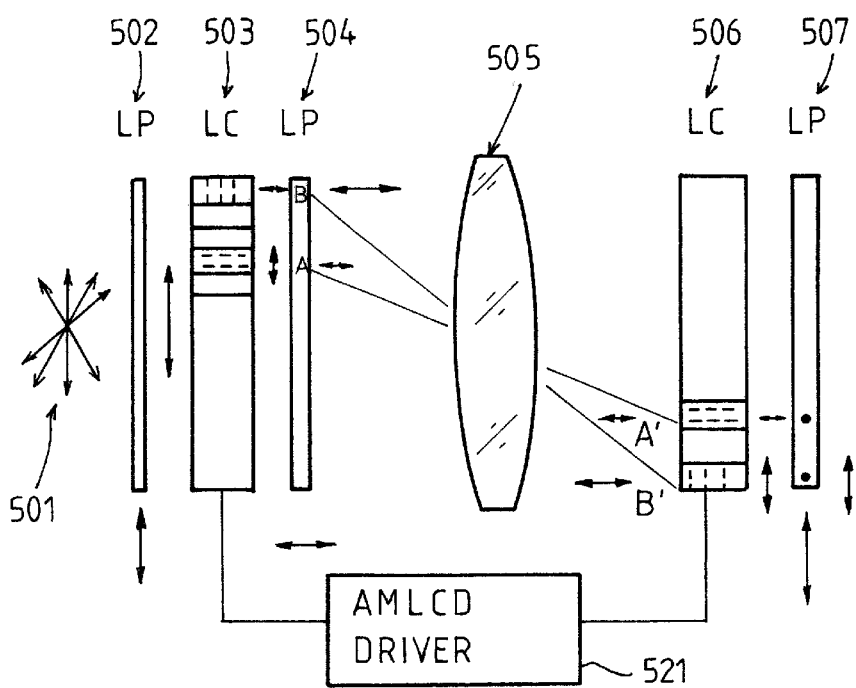
FIG. 5 shows a detailed block diagram of the micro display device shown in FIG. 4.

FIG. 5 shows a detailed block diagram of micro display device 400 shown in FIG. 4. As shown in FIG. 5, back illumination light 501 outputs randomly polarized light that passes through linear polarizer ("LP") 502. After passing through LP 502, illumination light 501 is linearly polarized, for example and for illustration only, parallel to the plane of the paper (P- polarization). The linearly polarized light then passes through LC 503 where the polarization is altered, on a pixel by pixel basis. Next, light emerging from LC 503 impinges upon linear polarizer ("LP") 504. LP 504 has its polarization axis oriented, for example, perpendicular to the plane of the paper (S-Polarization). Thus, it will pass S-polarized light, and it will block P-polarized light.

As shown in FIG. 5, LC 503 is controlled by AMLCD driver 521 which alters the amount of polarization change produced by individual pixels of LC 503. This is done by AMLCD 521 in response to output from a test pattern generator (not shown), which test pattern generator is typically included in AMLCD driver 521 (such AMLCD drivers are commercially available). As a result of this alteration, the polarization of light passing through LC 503 will be turned to different orientations, on a pixel-by-pixel basis. Only light having the proper polarization orientation will pass through LP 504. However, due to scattering and non-ideal polarization control of LC 503, light always leaks through the optical system, even if one wants to completely block the illumination light. This leakage is the cause of the low contrast ratio of prior art LC displays.

To increase the contrast ratio of an LC display in accordance with this embodiment of the present ratio, pixel array of LC 503 is imaged by lens system 505 to LC 506 so that LC 503 and LC 506 are optically conjugate. As a result, a pixel on LC 503 will be imaged to a pixel on LC 506. Although lens system 505 is shown as a single lens, those of ordinary skill in the art will readily understand that lens system 505 may comprise one or more lenses. Because light transmission of light through a Liquid Crystal light modulator pixel in its "on" state is high and light transmission through in its "off" state is low, the residual off-state light will be further blocked. In accordance with this embodiment of the present invention, LC 506 is driven synchronously with LC 503, and each pixel in the two Liquid Crystal light modulators is aligned and addressed precisely. The light emerging from LC 506 has its polarization altered and impinges on LP 507. LP 507 has its polarization axis parallel to the plane of the paper (i.e., the same as LP 502). Advantageously, the resulting contrast ratio of the combination will the square of the contrast ratio of LC 503 taken by itself.

Those skilled in the art will recognize that the foregoing description has been presented for the sake of illustration and description only. As such, it is not intended to be exhaustive or to limit the invention to the precise form disclosed.

What is claimed is:

1. A visual field tester that comprises:
   a high intensity light source;
   optical fiber;
   scanning optics;
   wherein light output from the light source is directed by the optical fiber to impinge upon the scanning optics, and the scanning optics directs the light to form a stimulus at various field positions; and
   a video display system that outputs one or more light patterns, and directs the output to impinge upon a subject's eye.

2. The visual field tester of claim 1 which further comprises a variable density filter disposed to vary the intensity of light output from the optical fiber.

3. The visual field tester of claim 2 wherein the variable density filter operates in response to a controller.

4. The visual field tester of claim 3 wherein the variable density filter comprises a variable neutral density filter wheel.

5. The visual field tester of claim 2 wherein the variable density filter comprises a variable neutral density filter and a color filter.

6. The visual field tester of claim 1 which further comprises viewing optics to magnify the field of view of the video display system and, together with at least a portion of the scanning optics, to magnify the field of view of the stimulus.

7. The visual field tester of claim 6 wherein the viewing optics includes an Erfle eyepiece.

8. The visual field tester of claims 1 wherein the light source is a high intensity white light source.

9. The visual field tester of claim 8 wherein the light source comprises a high intensity light box.

10. The visual field tester of claim 9 wherein the light box comprises a halogen lamp, a short arc mercury lamp, or a xenon lamp.

11. The visual field tester of claim 1 wherein the light source comprises a high brightness mini-CRT.

12. The visual field tester of claim 1 wherein the light source comprises a micro display device.

13. The visual field tester of claim 1 where the video display system outputs at least one of a uniform background, a frequency doubling type video pattern, and a visual resolution acuity test pattern.

14. The visual field tester of claim 13 wherein the video display system output is determined in response to input from a controller.

15. The visual field tester of claim 14 wherein the input from the controller is determined in response to user input.

16. The visual field tester of claim 1 wherein the scanning optics comprises a rotatable mirror.

17. The visual field tester of claim 16 wherein the rotatable mirror comprises is a gimbal-mounted mirror, and a pivot point thereof is imaged at a center of a subject's pupil.

18. The visual field tester of claim 1 wherein the scanning optics comprises a mechanism that translates an end of the optical fiber.

19. The visual field tester of claim 1 wherein the scanning optics comprises a translatable stage which translates an end of the optical fiber in response to signals from a controller.

20. The visual field tester of claim 19 wherein the scanning optics further comprises a wide angle, long eye relief, large exit pupil eyepiece lens.

21. The visual field tester of claim 20 wherein the eyepiece lens is an Erfle lens.

22. The visual field tester of claim 1 wherein the video display system outputs one or more light patterns in response to output from a controller.

23. The visual field tester of claim 1 which further comprises a color filter disposed between the optical fiber and the scanning optics.

24. The visual field tester of claim 20 wherein the color filter comprises a color filter wheel.

25. The visual field tester of claim 1 wherein a magnification of the scanning optics provides that a cross-sectional area of a core of the optical fiber subtends a 0.43 degree field of view at a subject's eye.

26. The visual field tester of claim 1 wherein the scanning optics comprises a lens system whose position along its optical axis is adjustable to enable the visual field tester to accommodate refraction error of a subject's eye.

27. The visual field tester of claim 1 wherein a numerical aperture of a core of the optical fiber and focal lengths of lens systems of the scanning optics provide a beam size of approximately 12 mm at a subject's cornea.

28. The visual field tester of claim 1 wherein the scanning optics further comprises an adjustable diaphragm.

29. The visual field tester of claim 1 wherein the video display system further composes a wide angle eye piece.

30. The visual field tester of claim 1 which further comprises a CCD camera optically conjugated to a subject's cornea.

31. The visual field tester of claim 1 wherein the scanning optics operates in response to input from a controller.

32. The visual field tester of claim 1 wherein the visual display system comprises a mini-CRT video display system, a liquid crystal display video display system, or a micro display device.

33. The visual field tester of claim 32 wherein the scanning optics comprises a wide angle lens system that is disposed to relay output from the video display system and the light source.

34. The visual field tester of claim 1 which further comprises a CCD camera optically conjugated to a subject's cornea.

35. A visual field tester that comprises:
a video display system that outputs one or more types of light patterns;
a background illumination display system; and
viewing optics to magnify the field of view of the video display system and the background illumination display system.

36. The visual field tester of claim 35 wherein the video display system comprises a high brightness mini-CRT.

37. The visual field tester of claim 35 wherein the video display system comprises a micro display device.

38. The visual field tester of claim 35 wherein the viewing optics comprises an inverted telephoto lens.

39. The visual field tester of claim 35 wherein the video display system outputs at least one of a frequency doubling type video pattern, and a visual resolution acuity test pattern.

40. The visual field tester of claim 39 wherein the video display system outputs one 6r more light patterns in response to output from a controller.

41. The visual field tester of claim 35 which further comprises a color filter disposed to intercept output from the video display system.

42. The visual field tester of claim 41 which further comprises a color filter disposed to intercept output from the background illumination display system.

43. The visual field tester of claim 35 wherein the background illumination system comprises a light box or a micro display device.

44. A visual field tester that comprises:
a video display system that outputs one or more light patterns; and
a background illumination display system that outputs variable intensity light;
wherein the video display system comprises:
a variable intensity, high brightness light source; and
a light modulator display disposed to transmit light output from the source.

45. The visual field tester of claim 44 which further comprises a controller to control the variable intensity, high brightness light source and the background illumination display system.

46. The visual field tester of claims 45 wherein the variable, high brightness light source comprises a high brightness light source and a variable neutral density filter.

47. The visual field tester of claim 46 wherein the high brightness light source comprises a liuorescent lamp, an LED array or a halogen lamp.

48. The visual field tester of claim 45 wherein the light modulator display comprises a liquid crystal based display system.

49. The visual field tester of claim 40 wherein the liquid crystal based display system comprises a micro display device.

50. The visual field tester of claim 48 wherein the liquid crystal based display system comprises a test pattern generator which operates in response to input from the controller.

51. The visual field tester of claim 45 wherein the controller produces output to cause a sum of background illumination from the video display system and from the background illumination display to have a predetermined value.

52. The visual field tester of claim 44 which further comprises an optical system to relay output from the video display system to a subject's eye, which optical system comprises a first lens system, wherein an entrance pupil of the first lens system is conjugated to a pupil of the subject's eye.

53. A micro display device which comprises:

alight source which outputs substantially polarized light;

a first liquid crystal display which transmits at least a portion of the polarized light;

a first polarizer which transmits light having a first direction of polarization;

a second liquid crystal display;

a relay optical system which relays light transmitted through the first liquid crystal display to the second liquid crystal display; and a second polarizer which transmits light having a second direction of polarization.

54. The micro display device of claim 53 wherein the light source comprises a source of unpolarized light and a polarizer.

55. The micro display device of claim 54 wherein the source of unpolarized light comprises a fluorescent lamp or an LED array.

56. The micro display device of claim 53 wherein the relay optical system has a 1:1 relay ratio.

57. The micro display device of claim 53 further comprises a test pattern generator that applies output to a driver, which driver applies output to the first and second liquid crystal displays.

* * * * *